(12) United States Patent
James, Jr.

(10) Patent No.: US 7,128,883 B2
(45) Date of Patent: Oct. 31, 2006

(54) PROCESS AND APPARATUS FOR ETHYLBENZENE PRODUCTION AND TRANSALKYLATION TO XYLENE

(75) Inventor: Robert B. James, Jr., Northbrook, IL (US)

(73) Assignee: UOP LLC, Des Plaines, IL (US)

(*) Notice: Subject to any disclaimer, the term of this patent is extended or adjusted under 35 U.S.C. 154(b) by 134 days.

(21) Appl. No.: 10/997,830

(22) Filed: Nov. 24, 2004

(65) Prior Publication Data
US 2005/0074376 A1    Apr. 7, 2005

Related U.S. Application Data

(62) Division of application No. 10/461,108, filed on Jun. 13, 2003, now Pat. No. 6,855,854.

(51) Int. Cl.
C07C 5/27   (2006.01)

(52) U.S. Cl. ............... 422/211; 422/217; 422/236; 585/323; 585/470; 585/475

(58) Field of Classification Search .......... 422/211, 422/217, 236; 585/323, 319, 470, 475
See application file for complete search history.

(56) References Cited

U.S. PATENT DOCUMENTS

| | | | |
|---|---|---|---|
| 3,130,007 A | 4/1964 | Breck | 23/113 |
| 3,216,789 A | 11/1965 | Breck et al. | 23/113 |
| 3,308,069 A | 3/1967 | Wadlinger et al. | 252/455 |
| 3,849,340 A | 11/1974 | Pollitzer | 252/455 Z |
| 4,083,866 A | 4/1978 | Petitpierre | 585/556 B |
| 4,169,111 A * | 9/1979 | Wight | 585/323 |
| 4,459,426 A | 7/1984 | Inwood et al. | 585/323 |
| 4,774,377 A * | 9/1988 | Barger et al. | 585/323 |
| 5,004,855 A | 4/1991 | Tada et al. | 585/489 |
| 5,030,786 A | 7/1991 | Shamshoum et al. | 585/467 |
| 5,177,285 A | 1/1993 | Van Opdorp et al. | 585/467 |
| 5,763,720 A | 6/1998 | Buchanan et al. | 585/475 |
| 5,847,256 A | 12/1998 | Ichioka et al. | 585/470 |
| 5,942,651 A | 8/1999 | Beech, Jr. et al. | 585/475 |
| 5,952,536 A | 9/1999 | Nacamuli et al. | 585/475 |
| 6,268,542 B1 * | 7/2001 | Merrill et al. | 585/643 |
| 6,342,649 B1 | 1/2002 | Winter et al. | 585/477 |
| 6,376,729 B1 * | 4/2002 | Merrill et al. | 585/449 |
| 6,855,854 B1 * | 2/2005 | James, Jr. | 585/323 |

OTHER PUBLICATIONS

*Handbook of Petroleum Refining Processes,* (Robert A. Meyers, 2d ed., 1997), pp. 2.3 to 2.11 by John J. Jeanneret.
Donald W. Breck, *Zeolite Molecular Sieves,* 1974, Robert E. Krieger Publishing Company, (pp. 122-124 and 162-163).

* cited by examiner

Primary Examiner—N. Bhat
(74) Attorney, Agent, or Firm—John G. Tolomei; Maryann Maas

(57) ABSTRACT

The use of two transalkylation catalysts to react aromatic compounds of carbon number nine (and heavier carbon numbers) with benzene to form carbon number eight aromatics is disclosed. The two catalyst system preserves ethyl-group species on the heavier aromatics that would otherwise de-ethylate over most gas-phase transalkylation catalysts to form undesired ethane gas with benzene or toluene. Thus, by using a transalkylation step to save ethylbenzene, a greater yield of para-xylene or other carbon number eight aromatics may be achieved within an integrated complex. An apparatus and process for the two transalkylation catalyst system is disclosed with a liquid-phase unit and a gas-phase unit.

20 Claims, 1 Drawing Sheet

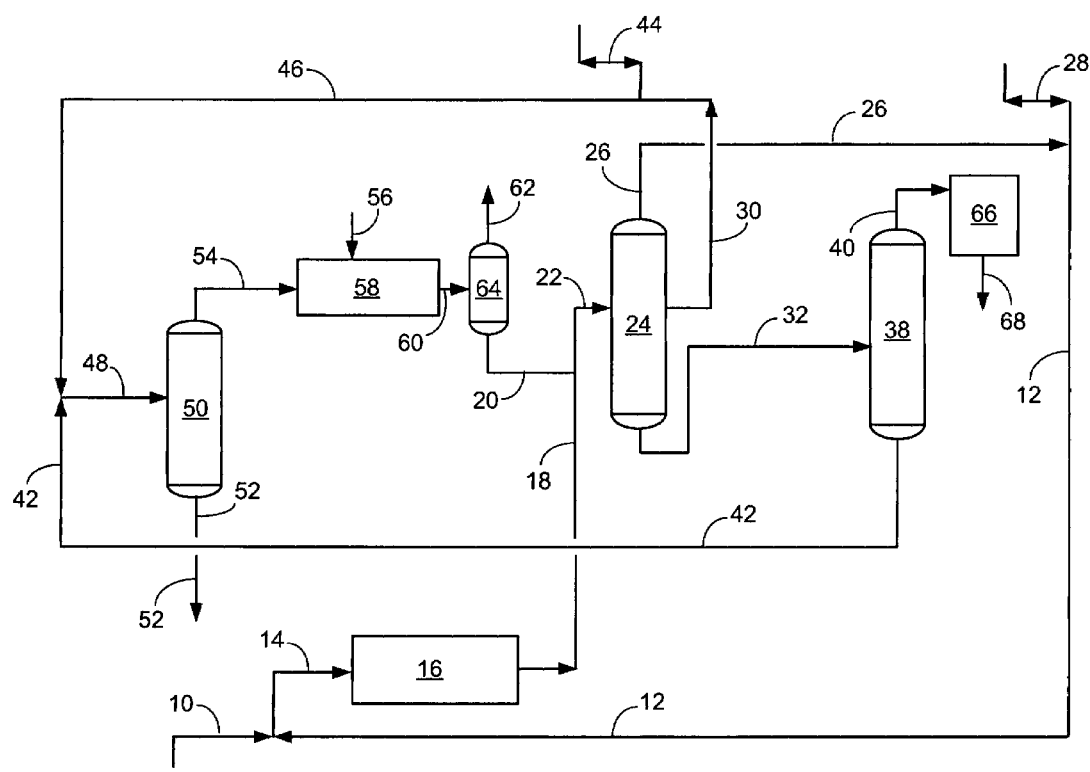

US 7,128,883 B2

PROCESS AND APPARATUS FOR ETHYLBENZENE PRODUCTION AND TRANSALKYLATION TO XYLENE

CROSS-REFERENCE TO RELATED APPLICATION

This application is a Division of application Ser. No. 10/461,108 filed Jun. 13, 2003, now U.S. Pat. No. 6,855,854 the contents of which are hereby incorporated by reference in its entirety.

FIELD OF THE INVENTION

This invention relates to an improved process for the conversion of aromatic hydrocarbons. More specifically, the present invention concerns a combination process for liquid-phase transalkylation of benzene with $C_9^+$ alkylaromatics to obtain ethylbenzene that would otherwise be lost via dealkylation to benzene or toluene in a subsequent gas-phase transalkylation process, thus obtaining a higher overall yield of xylenes.

BACKGROUND OF THE INVENTION

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene thus is a favorable objective, and processes to transalkylate $C_9$ aromatics and toluene have been commercialized to obtain high xylene yields.

U.S. Pat. No. 4,459,426 (Inwood et al.) discloses a liquid-phase transalkylation process, which is used in conjunction with an olefin alkylation process, that converts a poly-alkylaromatic mixture into additional mono-alkylaromatic compounds, such as ethylbenzene. This disclosure teaches that only trace amounts of xylenes, which are highly undesirable for such a process, are produced in amounts less than 0.2 wt-percent.

U.S. Pat. No. 5,004,855 (Tada et al.) discloses a process for ethylbenzene destruction within a $C_8$ alkylaromatic mixture. U.S. Pat. No. 6,342,649 B1 (Winters et al.) also discloses a method of removing ethylbenzene from a $C_8$ alkylaromatic mixture. Both of these disclosures teach conversion of the ethylbenzene component to benzene by irreversible de-ethylation.

Other types of transalkylation processes have been disclosed. U.S. Pat. No. 5,847,256 (Ichioka et al.) discloses a process for producing xylene from a feedstock containing $C_9$ alkylaromatics with ethyl-groups over a catalyst containing a zeolite component that is preferably mordenite and with a metal component that is preferably rhenium. U.S. Pat. No. 5,942,651 (Beech, Jr. et al.) discloses a flowscheme for a gas-phase transalkylation process in the presence of two zeolite containing catalysts to produce xylenes and benzene. The first catalyst contains a hydrogenation metal component and a zeolite component from the group including MCM-22, PSH-3, SSZ-25, ZSM-12, and zeolite beta. The second catalyst contains ZSM-5, and is used to reduce the level of saturate coboilers necessary for a high-purity benzene product. U.S. Pat. No. 5,952,536 (Nacamuli et al.) discloses a gas-phase transalkylation process using a catalyst comprising a zeolite from the group including SSZ-26, A1-SSZ-33, CIT-1, SSZ-35, and SSZ-44. The catalyst also comprises a mild hydrogenation metal such as nickel or palladium, and is used to convert aromatics with at least one alkyl group including benzene.

Economical processes in the field of integrated aromatics complexes are continually sought having exceptionally high selectivity for xylenes from other aromatic intermediates.

SUMMARY OF THE INVENTION

Accordingly, in one embodiment of the present invention, a process for transalkylation of benzene and $C_9^+$ alkylaromatics is integrated with a separate transalkylation process. The integrated process increases selectivity to xylenes by addressing the preservation of ethylbenzene in a first transalkylation unit that would otherwise be lost in a second transalkylation unit, thus resulting in a higher overall yield of valuable xylenes from both units. Preferably, the first transalkylation unit is substantially liquid-phase, while the second separate transalkylation process is substantially gas-phase.

In another embodiment of the present invention, the process is an apparatus for xylene production from light and heavier aromatics.

In yet another embodiment, the liquid-phase transalkylation process is integrated into a modem aromatic complex flow scheme to provide an increased yield of para-xylene isomer.

Additional objects, embodiments and details of this invention can be obtained from the following detailed description of the invention.

BRIEF DESCRIPTION OF THE DRAWINGS

The FIGURE schematically illustrates the major equipment used in performing the process of this invention. In the process $C_9^+$ alkylaromatics (called $A_9^+$) carried by a line 10 is admixed with benzene from a line 12 to form a combined line 14 and enters a transalkylation reactor 16. After contact with a zeolitic catalyst, a line 18 carries the effluent from the transalkylation reactor 16 to a combination point with a second transalkylation product stream in a line 20 to form a combined stream in a line 22 that enters a separation column 24. Separation column 24 separates the combined stream into an overhead of benzene taken by a line 26; a bottoms stream of $C_8^+$ alkylaromatics including ethylbenzene and xylene taken by a line 32; and a sidecut stream of toluene removed by a line 30. The overhead stream in line 26 is recycled back to transalkylation reactor 16 by line 12 after benzene is either removed or added via a line 28. The bottoms stream in line 32 is flowed to a second separation column 38 from which an overhead stream of ethylbenzene and xylene is taken by a line 40 and a bottom stream of $C_9^+$ alkylaromatics is withdrawn by a line 42. The ethylbenzene and xylene stream is sent via line 40 to a para-xylene production unit 66 to produce para-xylene by a line 68. The sidecut stream in line 30 is ultimately recycled to a second transalkylation reactor 58 by a line 46 after toluene is either removed or added via a line 44. Toluene in line 46 is admixed with line 42 to form a combined line 48 that enters a third separation column 50. Separation column 50 separates the combined stream into bottoms stream of $C_{11}^+$ alkylaromatics (called heavies) withdrawn by a line 52, and an overhead stream of $C_{10}$, $C_9$ alkylaromatics, and lighter compounds (including $C_7$ alkylaromatics) carried by a line 54 to second transalkylation reactor 58. Hydrogen is added to second transalkylation reactor 58 via a line 56. After contact with a transalkylation catalyst, a line 60 carries the effluent to a stabilizer column 64 from which an overhead stream of light end hydrocarbons (called light-ends gas, which generally comprises at least ethane) is taken by a line 62 and a bottom stream of second transalkylation product is withdrawn by line 20.

DETAILED DESCRIPTION OF THE INVENTION

The feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, di-isopropylbenzenes, and mixtures thereof.

The feed stream preferably comprises benzene and $C_9^+$ aromatics and suitably is derived from one or a variety of sources. The molar ratio of benzene to $C_9^+$ aromatics is preferably from about 0.5 to about 10. Feedstock may be produced synthetically, for example, from naphtha by catalytic reforming or by pyrolysis followed by hydrotreating to yield an aromatics-rich product. The feedstock may be derived from such product with suitable purity by extraction of aromatic hydrocarbons from a mixture of aromatic and nonaromatic hydrocarbons and fractionation of the extract. For instance, aromatics may be recovered from a reformate stream. The reformate stream may be produced by any of the processes known in the art. The aromatics then may be recovered from the reformate stream with the use of a selective solvent, such as one of the sulfolane type, in a liquid-liquid extraction zone. The recovered aromatics may then be separated into streams having the desired carbon number range by fractionation. When the severity of reforming or pyrolysis is sufficiently high, extraction may be unnecessary and fractionation may be sufficient to prepare the feedstock. Benzene may also be recovered from the product of transalkylation.

A preferred component of the feedstock is a heavy-aromatics stream comprising $C_9$ aromatics and $C_{10}$ aromatics. $C_{11}^+$ aromatics also may be present, typically in an amount of 50 wt-% or less of the feed. The heavy-aromatics stream generally comprises at least about 90 wt-% aromatics, and may be derived from the same or different known refinery and petrochemical processes as the benzene and toluene feedstock and/or may be recycled from the separation of the product from transalkylation.

The feedstock is preferably transalkylated in the liquid-phase and in the substantial absence of hydrogen. Substantial absence of hydrogen means without the addition of hydrogen beyond what may already be present and dissolved in a typical liquid aromatics feedstock. In the case of partial liquid-phase, hydrogen may be added in an amount less than 1 mole per mole of alkylaromatics. If the feedstock is transalkylated in the gas-phase, then hydrogen is added with the feedstock and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having increased xylene content of at least greater than 1 wt-% and also comprises ethylbenzene. When hydrogen is added to a transalkylation unit, the unit preferably comprises a recycle gas compressor to assist in recycling of hydrogen recovered from the reactor effluent in a separator vessel.

Generally, the use of two transalkylation zones will provide better results then the use of one transalkylation zone. Preferably, one zone will be liquid-phase and one zone will be gas-phase. Each transalkylation zone will continue to be described in generic terms below. Note that details of heat integration and additional flow details within the zones have not been shown in the schematic FIGURE because they are well known to the art.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stabilizer or stripping column in which substantially all $C_5$ and lighter hydrocarbons present in the effluent are concentrated into an overhead stream and removed from the process. An aromatics-rich stream is recovered as a net column bottoms stream which is referred to herein as the transalkylation effluent or transalkylation product.

To effect a transalkylation reaction, the present invention incorporates a transalkylation catalyst in at least one zone. Conditions employed in the transalkylation zone normally include a temperature of from about 100° to about 540° C. The transalkylation zone is operated at moderately elevated pressures broadly ranging from about 100 kPa to about 6 MPa absolute. The transalkylation reaction can be effected over a wide range of space velocities, with higher space velocities effecting a higher ratio of para-xylene at the expense of conversion. The weight hourly space velocity (WHSV) of the present invention generally is in the range of from about 0.1 to about 20 $hr^{-1}$. Preferably, these transalkylation conditions comprise a temperature from about 200° to about 300° C., a pressure from about 10 to about 50 kg/cm², and a weight hourly space velocity from about 0.5 to about 15 $hr^{-1}$.

The transalkylation effluent is separated into a light recycle stream, a mixed $C_8$ aromatics product and a heavy-aromatics stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the $C_9$ and heavier aromatics and may be partially or totally recycled to the transalkylation reaction zone.

One skilled in the art is familiar with several types of transalkylation catalysts that may be suitably used in the present invention. For example, in U.S. Pat. No. 3,849,340, which is herein incorporated by reference, a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver and zirconium. U.S. Pat. No. 4,083,866 is also incorporated by reference, and describes a process for transalkylation of alkylaromatic hydrocarbons that uses a zeolitic catalyst. Friedel-Crafts metal halides such as aluminum chloride have been employed with good results and are suitable for use in the present process. Hydrogen halides, boron halides, Group I-A metal halides, iron group metal halides, etc., have been found suitable. Refractory inorganic oxides, combined with the above-mentioned and other known catalytic materials, have been found useful in transalkylation operations. For instance, silica-alumina is described in U.S. Pat. No. 5,763,720, which is incorporated herein by reference.

Crystalline aluminosilicates have also been employed in the art as transalkylation catalysts. Examples of zeolites that are particularly suited for this purpose include, but are not limited to, zeolite beta, zeolite MTW, zeolite Y (both cubic and hexagonal forms), zeolite X, mordenite, zeolite L, zeolite ferrierite, MFI, and erionite. Zeolite beta is especially preferred and is described in U.S. Pat. No. 3,308,069 according to its structure, composition, and preferred methods of synthesis. Y zeolites are broadly defined in U.S. Pat. No. 3,130,007, which also includes synthesis and structural details. Mordenite is a naturally occurring siliceous zeolite which can have molecular channels defined by either 8 or 12 member rings. Donald W. Breck describes the structure and properties of mordenite in *Zeolite Molecular Sieves* (John Wiley and Sons, 1974, pp. 122–124 and 162–163). Zeolite L is defined in U.S. Pat. No. 3,216,789, which also provides information on its unique structure as well as its synthesis details. Other examples of zeolites that can be used are those having known structure types, as classified according to their three-letter designation by the Structure Commission of the International Zeolite Association ("Atlas of Zeolite Structure Types", by Meier, W. M.; Olsen, D. H; and Baerlocher, Ch., 1996) of MFI, FER, ERI, and FAU. Zeolite X is a specific example of the latter structure type that may be used in the present invention. The zeolite structure type MTW is also suitable.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica.

The zeolite may be present in a range from 5 to 99 wt-% of the catalyst and the refractory inorganic oxide may be present in a range of from about 5 to 95 wt-%. Preferred transalkylation catalysts are a type Y zeolite having an alumina or silica binder or a beta zeolite having an alumina or silica binder. Alumina is an especially preferred inorganic oxide binder.

The catalyst also contains an optional metal component. One preferred metal component is a Group VIII (IUPAC 8–10) metal, preferably a platinum-group metal, i.e., platinum, palladium, rhodium, ruthenium, osmium and iridium. Alternatively a preferred metal component is rhenium. Of the preferred platinum-group, platinum metal itself is especially preferred. This optional metal component may exist within the final catalytic composite as a compound such as an oxide, sulfide, halide, or oxyhalide, in chemical combination with one or more of the other ingredients of the composite, or, preferably, as an elemental metal. This component may be present in the final catalyst composite in any amount which is catalytically effective, generally comprising about 0.01 to about 2 wt-% of the final catalyst calculated on an elemental basis. The component may be incorporated into the catalyst in any suitable manner such as coprecipitation or cogelation with the carrier material, ion exchange or impregnation. Impregnation using water-soluble compounds of the metal is preferred, for example with chloroplatinic acid or perrhenic acid. Rhenium may also be used in conjunction with a platinum-group metal.

The catalyst may optionally contain a modifier component. Preferred metal modifier components of the catalyst include, for example, tin, germanium, lead, indium, and mixtures thereof. Catalytically effective amounts of such metal modifiers may be incorporated into the catalyst by any suitable manner. A preferred amount is a range of about 0.01 to about 2.0 wt-% on an elemental basis.

Generally, water may have a deleterious effect on the catalyst and prolonged contact with the catalyst will cause a loss of activity as described in U.S. Pat. No. 5,177,285 and U.S. Pat. No. 5,030,786. Thus, a typically low water concentration of less than about 200 wt-ppm results in reasonable operation.

An aromatics complex flow scheme has been disclosed by Meyers in the Handbook of Petroleum Refining Processes, 2d. Edition in 1997 by McGraw-Hill, which is incorporated by reference, based upon a conventional gas-phase transalkylation unit located within an integrated aromatics complex flow scheme designed for para-xylene production. Gas-phase herein means units that require addition of hydrogen, and generally contain hydrogen gas phase recycle loop systems around a reactor system.

An integrated aromatics complex will generally incorporate the transalkylation unit of the present invention along with a reforming unit, an alkyl-aromatic isomerization unit, a para-xylene separation unit, and an optional second transalkylation unit. The reforming unit will be used to generate the aromatic species that may be further separated in other units. Benzene is transalkylated in combination with $A_9^+$ aromatics to form xylenes and ethylbenzene in the transalkylation unit. Toluene may be further transalkylated in the optional second transalkylation unit to form additional xylenes in a transalkylation unit which are then processed in a loop comprising the isomerization and para-xylene separation units. The para-xylene separation unit may be either a crystallization or adsorptive based separation process well known to the art, which selectively removes the para-xylene in high purity while rejecting a non-equilibrium mixture of other xylenes and ethylbenzene. The non-equilibrium mixture, depleted in para-xylene, is contacted with an alkylaromatic isomerization catalyst in another process well-known in the art. The isomerization process re-equilibrates the mixture back to an equilibrium amount of para-xylene and converts ethylbenzene to xylenes which can be recycled back to the para-xylene separation unit for further recovery. Often the combination of a para-xylene separation unit and an alkylaromatic isomerization unit is called a 'loop'. This loop is defined herein as a 'para-xylene production' unit, wherein the loop produces para-xylene, which is recovered as a product from the process.

EXAMPLE

An increased selectivity to $A_8$s at the expense of light ends has been demonstrated in pilot plant tests and is shown in the following material balance comparison. The prior art, gas-phase transalkylation process, is compared against the present invention, which combines a liquid-phase transalkylation process with a gas-phase process. This comparison shows the benefits of the present invention as increased xylenes and ethylbenzene, and concomitantly decreased benzene and light-end gas (especially ethane). By reducing the production of ethane by de-ethylation in gas-phase reactions within an aromatics complex, the invention provides improved total retention of aromatics relative to prior art transalkylation units used in complexes that produce xylenes.

With reference to the FIGURE, showing the flow scheme of the present invention, a simulated material balance is shown below. The liquid-phase transalkylation process unit is combined with the gas-phase transalkylation process unit, and results in the following changes over a prior art single gas-phase transalkylation unit. Hydrogen feed to the flow scheme decreases. Feed of toluene and $A_9^+$ remains constant. Production of $A_8$s increases, while benzene production decreases. Heavies production remains constant. Most importantly, light-end gas production decreases.

These changes are summarized in the following table:

|  | Single Gas-phase Transalkylation Unit | Two Transalkylation Units (as shown in FIGURE) |
|---|---|---|
| Feed (kMTA) |  |  |
| $A_9^+$ | 151.7 | 151.7 |
| Hydrogen (H2) | 2.8 | 2.0 |
| Toluene | 151.7 | 151.7 |
| Total | 306.1 | 305.4 |
| Product (kMTA) |  |  |
| $A_8$ | 208.1 | 245.5 |
| Benzene | 53.1 | 25.8 |
| Light-end Gas | 33.4 | 22.6 |
| Heavies | 11.5 | 11.5 |
| Total | 306.1 | 305.4 |

Thus, the flow scheme of the present invention provides a benefit by producing more of the desirable $A_8$ material, which is the valuable xylenes and ethylbenzene.

What is claimed is:

1. A dual-transalkylation apparatus for conversion of aromatic hydrocarbons comprising:

a) a first-transalkylation unit comprising a liquid-phase reaction vessel, wherein benzene and $C_9^+$ alkylaromatics are contacted with a first-transalkylation catalyst under transalkylation conditions to produce a first-transalkylation product stream comprising ethylbenzene;

b) a first column, wherein the first-transalkylation product stream and a second-transalkylation product stream are separated to produce a fractionated-benzene stream and a xylene-plus stream;

c) a second column, wherein the xylene-plus stream is separated into a xylene-enriched stream, which is recovered as a product, and a $C_9^+$ alkylaromatic-enriched stream; and d) a second-transalkylation unit comprising a gas-phase reaction vessel, wherein a toluene feed stream is contacted with a second-transalkylation catalyst under transalkylation conditions to produce the second-transalkylation product stream.

2. The apparatus of claim 1 wherein the first-transalkylation catalyst comprises an inorganic oxide binder and a zeolitic aluminosilicate selected from the group consisting of MTW, MFI, type Y, beta, and mordenite.

3. The apparatus of claim 1 wherein the second-transalkylation catalyst comprises a zeolitic aluminosilicate selected from the group consisting of MTW, MFI, type Y, beta, and mordenite, an inorganic oxide binder, and an optional metal component.

4. The apparatus of claim 1 wherein the transalkylation conditions comprise a temperature from about 100° to about 540° C., a pressure from about 1 to about 60 kg/cm$^2$, and a weight hourly space velocity from about 0.1 to about 20 hr$^{-1}$.

5. The apparatus of claim 1 wherein the second-transalkylation unit further comprises a recycle gas compressor and a separator vessel.

6. The apparatus of claim 5 wherein the second-transalkylation unit further comprises a column, wherein the column produces a light gas comprising ethane.

7. The apparatus of claim 1 wherein the first column produces a toluene-enriched stream as a side-cut.

8. A dual-transalkylation apparatus for conversion of aromatic hydrocarbons comprising:

a) a first-transalkylation unit comprising a liquid-phase reaction vessel containing a first-transalkylation catalyst comprising an inorganic oxide binder and a zeolitic aluminosilicate selected from the group consisting of MTW, MFI, type Y, beta, and mordenite, wherein benzene and $C_9^+$ alkylaromatics are contacted under transalkylation conditions to produce a first-transalkylation product stream comprising ethylbenzene;

b) a first column, wherein the first-transalkylation product stream and a second-transalkylation product stream are separated to produce a fractionated-benzene stream, a xylene-plus stream, and a toluene-enriched stream;

c) a second column, wherein the xylene-plus stream is separated into a xylene-enriched stream, which is recovered as a product, and a $C_9^+$ alkylaromatic-enriched stream; and d) a second-transalkylation unit comprising a recycle gas compressor, a separator vessel, and a gas-phase reaction vessel containing a second-transalkylation catalyst comprising a zeolitic aluminosilicate selected from the group consisting of MTW, MFI, type Y, beta, and mordenite, an inorganic oxide binder, and an optional metal component, wherein at least part of the toluene-enriched stream is contacted under transalkylation conditions to produce the second-transalkylation product stream.

9. The apparatus of claim 8 wherein the transalkylation conditions comprise a temperature from about 100° to about 540° C., a pressure from about 1 to about 60 kg/cm$^2$, and a weight hourly space velocity from about 0.1 to about 20 hr$^{-1}$.

10. The apparatus of claim 8 wherein the second-transalkylation unit further comprises a column, wherein the column produces a light gas comprising ethane.

11. An integrated apparatus for producing para-xylene from aromatic hydrocarbons comprising:
   a) a first-transalkylation unit comprising a liquid-phase reaction vessel, wherein benzene and $C_9^+$ alkylaromatics are contacted with a first-transalkylation catalyst under transalkylation conditions to produce a first-transalkylation product stream comprising ethylbenzene;
   b) a first column, wherein the first-transalkylation product stream and a second-transalkylation product stream are separated to produce a fractionated-benzene stream and a xylene-plus stream;
   c) a second column, wherein the xylene-plus stream is separated into a xylene-enriched stream, and a $C_9^+$ alkylaromatic-enriched stream;
   d) a second-transalkylation unit comprising a gas-phase reaction vessel, wherein a toluene feed stream is contacted with a second-transalkylation catalyst under transalkylation conditions to produce the second-transalkylation product stream; and
   e) a para-xylene recovery section comprising a para-xylene separation unit, wherein the xylene-enriched stream of step (c) is concentrated into a para-xylene isomer enriched product stream which is recovered as a product stream of said apparatus.

12. The apparatus of claim 11 wherein the para-xylene separation unit is an adsorptive separation process or a fractional crystallization process.

13. The apparatus of claim 11 wherein the first-transalkylation catalyst comprises an inorganic oxide binder and a zeolitic aluminosilicate selected from the group consisting of MTW, MFI, type Y, beta, and mordenite.

14. The apparatus of claim 11 wherein the second-transalkylation catalyst comprises a zeolitic aluminosilicate selected from the group consisting of MTW, MFI, type Y, beta, and mordenite, an inorganic oxide binder, and an optional metal component.

15. The apparatus of claim 11 wherein the transalkylation conditions comprise a temperature from about 100° to about 540° C., a pressure from about 1 to about 60 kg/cm$^2$, and a weight hourly space velocity from about 0.1 to about 20 hr$^{-1}$.

16. The apparatus of claim 11 wherein the second-transalkylation unit further comprises a recycle gas compressor and a separator vessel.

17. The apparatus of claim 16 wherein the second-transalkylation unit further comprises a column, wherein the column produces a light gas comprising ethane.

18. The apparatus of claim 1 wherein the first column produces a toluene-enriched stream as a side-cut.

19. The apparatus of claim 11 wherein the para-xylene recovery section further comprises an alkylaromatics isomerization unit containing an alkylaromatic isomerization catalyst effective for conversion of ethylbenzene into para-xylene.

20. The apparatus of claim 19 further characterized wherein step (e) is a para-xylene production unit.

* * * * *